United States Patent [19]  [11] 4,436,745
York, Jr.  [45] Mar. 13, 1984

[54] METHOD OF INHIBITING ALDOSE REDUCTASE ACTIVITY

[75] Inventor: Billie M. York, Jr., Fort Worth, Tex.

[73] Assignee: Alcon Laboratories, Inc., Fort Worth, Tex.

[21] Appl. No.: 368,630

[22] Filed: Apr. 15, 1982

[51] Int. Cl.$^3$ .......................................... A61K 31/415
[52] U.S. Cl. ................................................ 424/273 R
[58] Field of Search ..................... 424/273 R; 548/308

[56] References Cited

U.S. PATENT DOCUMENTS

| | | | |
|---|---|---|---|
| 2,683,718 | 7/1954 | Dornfeld et al. | 260/309.5 |
| 2,716,648 | 8/1955 | Jules et al. | 260/309.5 |
| 3,349,124 | 10/1967 | McLamore | 260/553 |
| 3,532,744 | 10/1970 | Fletcher et al. | 260/518 |
| 3,821,383 | 6/1974 | Sestanj et al. | 424/258 |
| 4,117,230 | 9/1978 | Sarges | 548/309 |
| 4,127,665 | 11/1978 | Sarges et al. | 424/273 R |
| 4,130,714 | 12/1978 | Sarges | 548/309 |
| 4,147,795 | 4/1979 | Sarges | 424/273 R |
| 4,147,797 | 4/1979 | Kelbaugh et al. | 424/273 R |
| 4,181,728 | 1/1980 | Sarges et al. | 424/273 R |
| 4,181,729 | 1/1980 | Sarges et al. | 424/273 R |
| 4,200,642 | 4/1980 | Schnur | 424/272 |
| 4,209,630 | 6/1980 | Sarges | 548/309 |
| 4,307,108 | 12/1981 | Belletire et al. | 424/274 |
| 4,327,107 | 4/1982 | Cale, Jr. | 424/273 R |

FOREIGN PATENT DOCUMENTS 1135915 6/1961 Fed. Rep. of Germany .

OTHER PUBLICATIONS

McCown et al., JACS 64, 689, (1942).
Pan et al., J. Med. Chem., 7, 31–38, (1964).
Pan et al., J. Med. Chem., 7, 10, 957–959, (1967).
Clements, "Neuropathy in Young Diabetics".
Organic Synthesis, vol. 2, p. 447.
Sprinzak, JACS 80 5449, (1958).
Fletcher, J. Org. Chem., 25 1342, (1960).
Goodson, J. Org. Chem. 25 1920, (1960).
Fletcher, Chem. & Indus. Feb. 11, 1961, p. 179.
Parry, JACS 4049–4054, (1965).
Bavin, Organic Synthesis 5 30.
Abstracts #119 and #120.
Chem. Abstracts, vol. 80, p. 398.
Pendergast, J. of Biochem. 25 1282.
Granoth et al., J. Org. Chem. 40 2088.
McGilvey, Biochemistry, A Functional Approach, pp. 631–632, Saunders, Philadelphia, Pa., (1970).
Stewart et al., "Polyol Accumulations in Nervous Tissue of Rats with Experimental Diabetes and Galactosemia", J. of Neurochemistry, 14 1057–1066, (1967).

*Primary Examiner*—Leonard Schenkman
*Attorney, Agent, or Firm*—Fitch, Even, Tabin & Flannery

[57] ABSTRACT

Inhibition of aldose reductase activity with tetracyclic spiro-hydantoins.

18 Claims, No Drawings

METHOD OF INHIBITING ALDOSE REDUCTASE ACTIVITY

This invention relates to the method of inhibiting aldose reductase activity with hydantoin derivatives. This invention particularly concerns the use of spirohydantoin compounds with a substituted and unsubstituted fluorene ring in the treatment of complications arising from diabetes mellitus such as cataracts and neuropathy.

In diabetes mellitus certain tissues are subject to exposure to high glucose levels. In the lens of the eye, nerves, kidney, retina and other tissues is the enzyme aldose reductase. The latter is mainly responsible for the reduction of aldoses such as glucose to a polyol such as sorbitol and galactose to galactitol at the expense of NADPH. Accumulations of sorbitol in diabetic subjects cause and/or are associated with diabetic complications including those of a lenticular, reninal, neuronal and renal nature. These complications are generally known as diabetic cataract, retinopathy, neuropathy, and nephropathy respectively. Elevated polyol such as sorbitol or galactitol in the eye lens lead to cataract and loss of lens transparency. Elevated polyol such as sorbitol in the peripheral nerves interferes with normal nervous function. Aldose reductase action on elevated glucose and/or galactose is also implicated in causing vasculature basement membrane thickening per se in the retinal capillaries and certain kidney tissues. Aldose reductase inhibitors inhibit the activity of aldose reductase. Hence, aldose reductase inhibitors prevent the production of polyols which directly or indirectly lead to the formation of cataracts, reduced nerve conduction/function, and some diabetic vasculature pathophysiology.

K. Sestanj et al. in the U.S. Pat. No. 3,821,383 discloses 1,3-dioxo-1H-benz-[d,3]-isoquinoline-2(3H)-acetic acid and derivatives thereof as aldose reductase inhibitors. Further, the search for effective antidiabetic agents to prevent or arrest chronic complications such as cataracts, neuropathy and retinopathy has revealed that particular spiro-hydantoin compounds are useful as aldose reductase inhibitors.

Sarges U.S. Pat. No. 4,117,230 describes a series of spiro-hydantoin compounds which include the 6-fluoro and 6,8-dichloro derivatives of spiro-chroman-imidazolidinediones.

Sarges U.S. Pat. No. 4,130,714 describes enhanced activity of specific dextrotatory spiro-hydantoin compounds such as d-spiro-[6-fluoro-chroman-4,4'-imidazolidine]-2',5'-dione and d-spiro-[6'-fluoro-imidazolidine-4,4'-thiochroman]-2,5' dione in preventing selected diabetic complications.

Sarges et al. U.S. Pat. Nos. 4,181,728 and 4,181,729 describe spiro-polycyclicimidazolidinedione derivatives and phenyl or phenoxy substituted spiro-imidazolidinedione derivatives, respectively, which are useful to inhibit the enzymatic reduction of aldoses to prevent or reduce harmful and unwanted accumulations of polyols in the lens and nerves.

Methythio and methylsulfinyl (also called methylsulfoxyl) substituted spiro-chroman-imidazolidinediones which are the subject of a contemporaneously filed application also are useful as aldose reductase inhibitors. With respect to sulphur containing derivatives in the instant invention, a methylsulfinyl derivative of spiro-[fluoren-9,4'-imidazolidine]-2',5'-dione may be biotransformed in vivo to the corresponding more active methylthio derivative. There can be an interconversion of the sulfoxide to the sulfide by thioredoxin-dependent reductases and/or related glutaredoxins. In the converse, the methylthio derivative can be oxidized by cytochrome containing oxidoreductases to the corresponding methylsulfinyl derivative. These interconversions can be stereospecific with respect to the chirality of the resulting sulfoxide. Other sulfoxide or sulfinyl drugs such as Sulindac have been demonstrated to undergo these biotransformations as a function of drug intermediary metabolism. Therefore it is believed that the less in vitro active methylsulfinyl derivatives will exhibit greater than expected in vivo activity because of this intermediary metabolism.

In accordance with the present invention it has been found that compounds of the formulas:

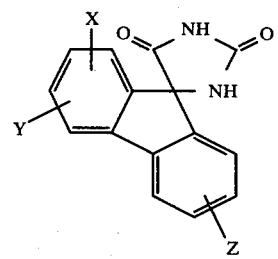

where x, y and z are hydrogen, halogen, methyl, methylthio, methylsulfinyl, methoxyl, methylsulfonyl and salts thereof with pharmacologically acceptable cations may be employed as aldose reductase inhibitors for the control and prevention of sorbitol levels in the sciatic nerve and lens of diabetics, to reduce sorbitol levels in the lens of glucosemic subjects with resulting control of diabetic complications including diabetic cataracts, and to generally treat diabetic complications including diabetic cataract, neuropathy, retinopathy and nephropathy. The pharmaceutically acceptable metallic salts can be prepared from the corresponding unneutralized derivatives using conventional methods. Treatment of a derivative with an aqueous solution of the desired pharmaceutically acceptable metallic hydroxide or other metallic base and evaporation of the resulting solution to dryness, usually under reduced pressure, will yield the salt. These compounds are unique over the prior art in that they contain a tricylic ring system which is rigid and planar in conjunction with a heterocyclic ring.

The substantial increase in activity and potency of the aforedescribed tetracyclic spiro-hydantoin derivatives as seen over known compounds by in vitro and in vivo assays is unanticipated. Prior art does not indicate such unanticipated increase in the activity and potency of such planar, rigid, tetracylic spiro-hydantoin derivatives. Further, the compounds are more active in vitro and in vivo than material found in the prior art and are anticipated to have characteristics that will provide useful in vivo human activity and potency. Furthermore, several of the potent symmetrically substituted derivatives do not require resolution as they are achiral.

It will be understood that these tetracylic spiro-hydantoin derivatives will contain an asymmetric center if the substitution pattern on rings A and C are not symmetric. It is known in the art that for this class of molecules, a resolved compound is more potent than an unresolved compound. For example, a 2-fluoro substitution renders the molecule asymmetric at the 9-position of the fluorene ring as the same carbon atom at position 4' in the spiro hydantoin ring D. A 2,7-difluoro, 2,7-dibromo, etc., substitution pattern results in a symmetric molecule and hence no resolution is needed for an increase in activity and potency.

It has also been found that tetracyclic spiro-xanthene-imidazolidines such as spiro-(2,7-difluroxanthen-9,4'-imidazolidine)-2',5'-dione and spiro-(xanthen-9,4'-imidazolidine)-2',5'-dione are unexpectedly less active as aldose reductase inhibitors and are not as potent as the corresponding tetracyclic fluorene compounds of the invention disclosed herein.

PREPARATION A

Spiro-(fluoren-9,4'-imidazolidine)-2',5'-dione has the formula:

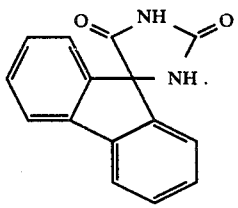

Spiro-[fluoren-9,4'-imidazolidine]-2',5'-dione was prepared by the general method of W. H. McCown and H. R. Henze as reported in *J. Amer. Chem. Soc.* 64, (1942) 689. Fluorenone (9 g, 50 mmol.), KCN (6.5 g, 100 mmol), ammonium carbonate (22.8 g) and 80% ethanol (100 mL) were placed in a 200 cc stainless steel reaction vessel. The mixture was heated at 115°–125° C. for 4.0 hours, cooled and diluted with ice cold 10% hydrochloric acid. The triturated solid was collected on the filter, washed with water and dried to yield 11.8 g (95%), m.p. 326°–329° C. dec. Recrystallization from ethanol yielded needles, m.p. 350°–353° C. dec., m/e+· 250 for $C_{15}H_{10}N_2O_2$.

PREPARATION B

Spiro-[2,7-dichlorofluoren-9,4'-imidazolidine]-2',5'-dione has the formula

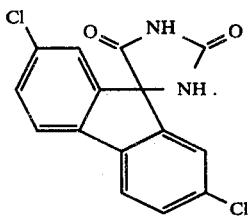

This compound was prepared by the method of Hsi-Lung Pan and T. L. Fletcher, *J. Med. Chem.* 10 (1967), 957–959. Spiro-[fluoren-9,4'-imidazolidine]-2',5'-dione (5 g, 20 mmol), FeCl₃ (0.5 g) and acetic acid (350 mL) was stirred at 75° C. while a solution of Cl₂ (3.6 g, 50 mmol) in acetic acid (60 mL) was added in one portion. The mixture was stirred with heat for twenty four hours. After cooling water was added and the product filtered. Recrystallization from ethanol gave 0.9 g of product (14%); m.p. 355°–358° C. dec.; m/e+· 318 for $C_{15}H_8Cl_2N_2O_2$.

PREPARATION C dl-Spiro-[2-nitrofluoren-9,4'-imidazolidine]-2',5'-dione has the formula

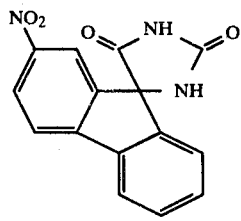

and may be prepared as follows.

Powdered spiro-[fluoren-9,4'-imidazolidine]-2',5'-dione (5.0 g, 20 mmol) was added to a stirred mixture of HNO₃ (2 g, 22 mmol) and 60% H₂SO₄ (100 mL) at 5° C. Then the mixture was allowed to cool to room temperature and was stirred for twelve hours, ice water was added and the solid was filtered. Recrystallization from acetic acid gave a sample, m.p. 309°–312° C. dec., m/e+· 295 for $C_{15}H_9N_3O_4$.

PREPARATION D

Spiro [2,7-dinitrofluoren-9,4'-imidazolidine]-2',5'-dione has the formula

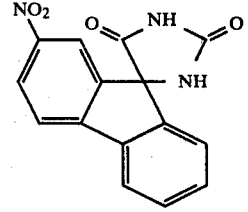

It may be prepared according to Hsi-Lung Pan and T. L. Fletcher, *J. Med. Chem* 10, (1967) 957–959. Powdered spiro-[fluoren-9,4'-imidazolidine]-2',5'-dione (6.0 g) was added to a stirred mixture of HNO₃ (10 g) and 60% H₂SO₄ (100 mL) at 50°–60° C. over a period of 45 minutes. The suspension was stirred at the same temperature for 5 hours and cooled. Cold water was added and the solid was filtered. Several recrystallizations from acetic acid gave a sample, m.p. 333°–335° C. dec., m/e+· 340 for $C_{15}H_8N_4O_6$.

PREPARATION E dl-Spiro-[2-bromofluoren-9,4'-imidazolidine]-2',5'-dione has the formula

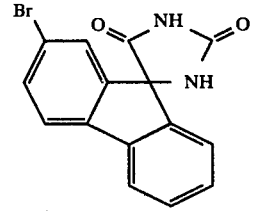

It may be prepared according to H. L. Pan and T. L. Fletcher, *J. Med. Chem.* 10, (1967) 957–959. 2-Bromofluorene (Trans World Chemicals, Inc.) was oxidized by sodium dichromate to 2-bromofluorenone. The product, yellow needles, recrystallized from ethanol gave a m.p. 146°–147° C. The ketone (2.6 g, 10 mmol), KCN (1.3 g, 20 mmol), ammonium carbonate (5.0 g) and 80% ethanol (100 mL) were placed in a stainless steel reaction vessel. The mixture was heated at 115°–125° C. for 4.0 hours. The product was collected as in Preparation A and recrystallized from ethanol to yield white needles (2.7 g), m.p. 350°–353° C., m/e+· 328 for $C_{15}H_9BrN_2O_2$.

PREPARATION F

Spiro-[2,7-dibromofluoren-9,4'-imidazolidine]-2',5'-dione has the formula

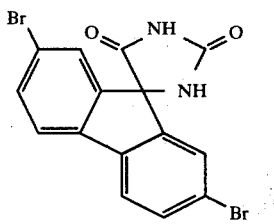

and may be prepared as follows.

To 2,7-dibromofluorene (1.5 g, 4.6 mmol) in pyridine (50 mL) was added potassium permanaganate (0.73 g, 4.6 mmol) and the mixture was stirred overnight. Alcohol (10 mL) was added and then water 100 ml and the mixture was extracted with ether (100 mL, twice). The combined extracts were washed with two portions of 5% hydrochloric acid (20 mL each) and water (50 ml). The ether was evaporated to yield 1.2 g of the ketone needles from benzene, m/e+· 334 for the ketone, m.p. 196°–197° C. for $C_{13}H_6Br_2O$. The ketone (1.2 g, 3.6 mmol), KCN (0.468, 7 mmol) and ammonium carbonate (1.36 g) in alcohol (15 mL) were heated at 105° C. overnight in a stainless steel pressure reactor. The product was collected as in Pocedure A, the product having a m.p. 340° C., m/e+· 406 for $C_{15}H_8N_2O_2Br_2$.

PREPARATION G dl-Spiro-[4-aminofluoren-9,4'-imidazolidine]-2',5'-dione has the formula

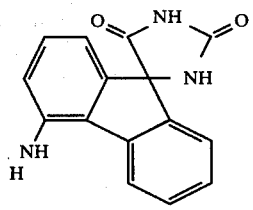

and may be prepared as follows.

4-Amino-fluorenone (Pfaltz and Bauer, Inc.) (5 g, 19 mmol), KCN (3.33 g, 51 mmol), ammonium carbonate (9.9 g) in 95% alcohol (50 mL) were heated in a glass pressure reactor at 105° C. for 24 hours. The cooled reaction mixture was poured into 400 ml cold water and adjusted to pH 5 with hydrochloric acid. The precipitate was filtered and redissolved in 5% NaOH solution (100 mL) and refiltered through a Celite pad. Once again the pH was adjusted to an acid pH and the solid collected; recrystallization from hot methanol yielded a product m.p. 340°–342° C.; m/e+· 265 for $C_{15}H_{11}N_3O_2$.

PREPARATION H dl-Spiro-[2-aminofluoren-9,4'-imidazolidine]-2',5'-dione has the formula

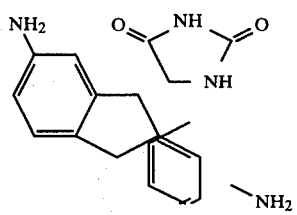

and may be prepared as follows.

2-Aminofluorenone (Aldrich Chemical Co., Inc.) (1.95 g, 10 mmol), KCN (1.0 g, 15 mmol), ammonium carbonate (2.0 g) and 90% ethanol (50 mL) were heated in a glass pressure reactor at 105° C. for 24 hours. The cooled reaction mixture was poured into 100 mL cold water and the pH was adjusted to 5 with 10% hydrochloric acid; the precipitate was filtered and redissolved in 5% NaOH (50 mL) and refiltered. Once again the pH was adjusted to an acid pH and solid collected. Recrystallization from hot methanol yielded a product m.p. 310°–314° C. m/e+· 265 for $C_{15}H_{11}N_3O_2$.

PREPARATION I

Spiro-[2,7-diaminofluoren-9,4'-imidazolidine]-2',5'-dione has the formula

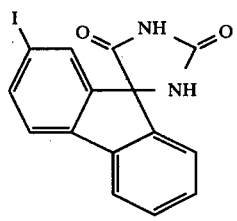

and may be prepared as follows.

Spiro-[2,7-dinitrofluoren-9,4'-imidazolidine]-2',5'-dione (4.5 g, 13 mmol) was suspended in 1 liter reagent alcohol. A stirred suspension of 85% hydrazine hydrate (25 mL) and Raney nickel (1 g) was added. The mixture was refluxed for two hours and filtered. The filtrate was evaporated to yield a light brown solid. The product was recrystallized from ethanol, m.p. 340°–344° C. dec., m/e+· 280 for $C_{15}H_{12}N_4O_2$; HRMS for $C_{15}H_{12}N_4O_2$: calc. 280.0960, obs. 280.0951, error 0.9 mmu/3.2 ppm.

PREPARATION J dl-Spiro-[2-iodofluoren-9,4'-imidazolidine]-2',5'-dione has the formula and may be prepared as follows.

2-Iodofluorenone (Aldrich Chemical Co.) (4.0 g, 13 mmol), KCN (1.7 g, 30 mmol), ammonium carbonate (6.0 g) in 90% ethanol (60 mL) was placed in a stainless steel reaction vessel. The mixture was heated at 110°–115° C. for 12 hours. The reaction vessel was cooled, and cold 10% hydrochloric acid was added. The precipitate was collected by filtration. The solid was dissolved in 5% sodium hydroxide and reprecipitated with cold 10% hydrochloric acid. The collected solid was recrystallized from acetone and water to yield fine crystals, m.p. 358°–359° C., m/e+· 376 for $C_{15}H_9IN_2O_2$.

PREPARATION K dl-Spiro-[1-methylfluoren-9,4'-imidazolidine]-2',5'-dione has the formula

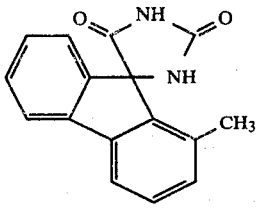

and may be prepared as follows.

1-Methylfluorenone (2 g, 13 mmol), KCN (1.7 g, 26 mmol), ammonium carbonate (5.1 g) and 95% ethanol (50 mL) were placed in a glass pressure reactor and heated overnight. The reaction mixture was diluted with 200 mL 5% hydrochloric acid solution and the product was collected on a filter. The product was then dissolved in 5% NaOH solution (150 mL); refiltered; reprecipitated with conc. hydrochloric acid. This product was recrystallized from hot methanol; yield 1.5 g; m.p. 334°–336° C. dec.; m/e+· 264 for $C_{16}H_{12}N_2O_2$.

PREPARATION L dl-Spiro(2-fluorofluoren-9,4'-imidazolidine)-2',5'-dione has the formula:

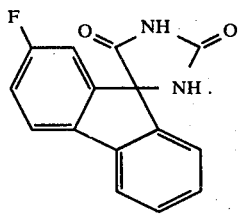

Fluoroboric acid (3000 ml, 48–50%) is diluted with water (1500 mL) and chilled. 2-Aminofluorene (Aldrich Chemical Co.) (543.7 g, 3 mol) in tetrahydrofuran (1500 ml) was portion wise added with stirring to the chilled fluorboric acid solution (4500 mL). A pink-brown solid formed during addition. The mixture was stirred until it became homogenous and then was chilled to approximately 5° C. with dry ice in an acetone bath. A saturated aqueous solution of sodium nitrite (300 g with water to yield 600 cc of solution) was added dropwise while at 3°–8° C. After the addition, the mixture was stirred for one hour. The insoluble green product was collected by filtration and washed with 5% flouroboric acid (3×200 mL), methanol (300 mL), 15% methanol in ether (5×200 mL), ether (5×200 mL) and then air dried overnight to yield the diazonium salt (809 g, 97%), m.p. 133°–135° dec. The diazonium salt (800 g) was suspended in xylenes (3000 mL) with stirring. The mixture was heated to boiling. As the temperature became 100° C. nitrogen gas evolved and subsided as the temperature became 135° C. The boiling mixture was filtered hot through a Celite (a diatomaceous filter aid) pad and the pad was washed with hot xylenes (3×200 mL). The combined filtrates were evaporated in vacuo with heat to dryness. The residue was dissolved in boiling hexanes (3000 mL) then filtered through a Celite and Norite (neutralized charcoal) filter pad with hot hexanes wash (400–600 mL). The combined hexanes filtrate then were cooled with dry ice. The resulting white precipitate was collected by filtration. The collected product was washed with cold hexanes (200 mL), suction dried and oven dried at 50° C. to yield 2-fluorofluorene (380 g, 71.7%) with a m.p. 97.5°–98.0° C. A second crop of product was collected by concentrating the hexanes mother liquor, cooling and collecting the precipitate as before (total combined yield 416 g).

2-Fluorofluorene (824.7 g, 4.48 mol) was dissolved in pyridine (4 L) and stirred. A 40% solution of Triton B (100 mL of benzyltrimethylammonium hydroxide 40% in pyridine according to a general procedure of U. Sprinzak, J. Amer. Chem. Soc. 80 (1958) 5449) was added and oxygen was bubbled into the vigorously stirred solution. This exothermic reaction was run for 20 hours whereupon an additional portion of the Triton B solution (50 mL) was added with continued stirring and oxygen addition for an additional 24 hours. The resulting dark green reaction mixture was treated with Norite (100 g, neutralized charcoal), stirred for 30 minutes and filtered through a Celite pad. The filter pad was then washed with pyridine (1 L). The combined filtrates were concentrated to a small volume in vacuo with heat. A 5% solution of hydrochloric acid in water (1 L) was added and the pyridine was azeotrophed in vacuo with heat. This process was repeated until a total of 6–8 L of water were evaporated. The granular product was filtered and washed with water (4 L) and air dried. The yellow-orange product was distilled through a large bore short path distillation apparatus (bp 167°–170° C.; 1.5 mm Hg) to yield into a chilled receiving flask the bright yellow 2-fluorofluorenone (600 g) with a m.p. 113°–115° C. and m/e+· 198 for $C_{13}H_7FO$.

2-Fluorofluorenone (300 g, 1.52 mol), ammonium carbonate (420 g) and potassium cyanide (120 g, 1.84 mol) were suspended in absolute ethanol (1.2 L) in a 2 L stainless steel Parr pressure reaction apparatus. The sealed vessel was heated at 95°–100° C. with mechanical stirring over 42–46 hours. The contents of the 2 L vessel was transferred into water (4 L). The yellowish water mixture was made acidic by the slow addition of concentrated hydrochloric acid (500 mL) so as to be pH2. The resulting precipitate was collected by filtration, washed with water (4 L) and suction dried. The damp solid was partially solubilized with 1 N sodium hydroxide (1.5 L) by stirring. The insolubles were removed by filtration through a Celite filter aid and neutralized charcoal pad to obtain a clear solution. The pad was washed with 1 N sodium hydroxide (1.0 L). The combined filtrates were acidified as before with conc. hydrochloric acid (about 200 mL) to pH2. The white precipitate was collected by filtration, washed with water (4 L), suction dried, and washed with ether (4×300 mL). The damp solid then was dried at 100° C. for 12 hours to yield dl-spiro-(2-fluorofluoren-9,4'-imidazolidine)-2',5'-dione (301 g, 74.3%), 284 g of this product was dissolved in dimethylformamide (600 mL) at 40° C. Norite (40 g, neutralized charcoal) was added to the solution and the mixture stirred at 45° C. for 40 min. The mixture was filtered through a Celite pad and the filtrate was diluted with water (2 L). The solid was collected by filtration with water wash (500 mL). The damp solid was dissolved in 1 N sodium hydroxide (1 L) and treated with Darco G-60 (Fisher Scientific activated charcoal for chromatography) and stirred for 35 min. at 30° C. The mixture was filtered through a carefully prepared Celite pad with 1 N sodium hydroxide solution wash (500 mL) and water wash (1 L). The combined filtrates (2.5 L) were neutralized with concentrated hydrochloric acid to pH 6.5. The white precipitate was collected by filtration and was washed with water, air dried and oven dried at 100° C. for 24 hrs. to yield (273 g) of dl-spiro-(2-fluorofluoren-9,4'-imidazolidine)-2',5'-dione.

A sample of the product, which was recrystallized from ethanol, gave a m.p. 315° C. with decomposition, HRMS analysis for $C_{15}H_9FN_2O_2$ calc. 268.0648, obs. 268.0659; error 1.1 mmu/4.1 ppm; $C_{15}H_9FN_2O_2$, calc %C 67.15 %H 3.38 %N 10.45 %F 7.08, obs. %C 67.24 %H 3.56 %N 10.42 %F 7.22, obs. %C 67.17 %H 3.42 %N 10.41 %F 6.98, obs. %C 67.29 %H 3.47 %N 10.50 %F 7.27, obs. %C 67.26 %H 3.35 %N 10.41 %F 7.03; IR Spectrum: 3270 cm$^{-1}$ N-H stretch of II° imide, 3170 cm$^{-1}$, N-H stretch of imide, 3050 cm$^{-1}$, Sp$^2$ C-H stretch, 1775 cm$^{-1}$, C=O stretch of imide, 1715 cm$^{-1}$ C=O stretch of imide and amide, 1610, 1590, 1495 and 1455 cm$^{-1}$ aromatic in-plane carbon stretching modes, 1422 cm$^{-1}$ N-H in-plane bend of II° cyclic amide, 868, 830 and 752 cm$^{-1}$ aromatic C-H out-of-plane deformation, and NMR Spectrum Assignments: delta 11.3 ppm: broad singlet, 1H, imide proton; 8.7 ppm: broad singlet, 1H, amide proton; 7.9 ppm: multiplet, 2H, aromatic protons; 7.4 ppm: multiplet, 5H, aromatic protons.

PREPARATION M

Sprio-[2,7-difluorofluoren-9,4'-imidazolidine]-2',5'-dione has the formula:

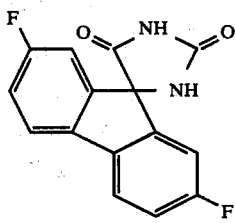

can be prepared from 2,7-difluorofluorene which can be obtained from the Alfred Bader Library of Rare Chemicals. Alternatively, 2,7-difluorofluorene may be prepared in accordance with the following procedure. To 2,7-diaminofluorene (Aldrich Chemical Co.) (4.98 g, 25.4 mmol) in tetrahydrofuran (90 mL) was added water (25 ml) and fluoroboric acid (48–50%, 50 mL). A thick paste of the fluoroborate salt formed. While stirring and cooling (5° C.), a saturated aqueous solution of sodium nitrite (5 g) was added dropwise while maintaining the temperature at 5°–10° C. After addition, the mixture was stirred for ten minutes and filtered and washed with 5% fluoroboric acid, methanol and then ether. The dried product, the bis-diazonium salt, decomposed at 127° C. The salt product was then mixed with boiling xylenes (50 mL) and heated for 30 minutes yielding a dark tar material, 5.1 g. The tar was isolated and triturated with ether. The ether was evaporated and the product, 2,7-difluorofluorene, was recrystallized from ethanol, 3.9 g, m.p. 80°–82.5° C. The 2,7-difluorofluorene (2 g, 10 mmol) was dissolved in pyridine (30 mL) and potassium permanganate (1.58 g) was added and stirred at room temperature overnight. The reaction mixture was diluted with water and then acidified with 5% HCl. The solid was filtered and water washed. The solid was suspended in 100 mL water and a solution of saturated sodium bisulfite and concentrated hydrochloric acid (7.27 g NaHSO$_3$, 6.90 g of conc. HCl) was added and the mixture stirred for thirty minutes. The solid was collected by filtration and then dissolved in ether and refiltered. The ether extracted ketone product 2,7-difluorofluorenone (0.9 g) gave m/e+ 216.

2,7-Difluorofluorenone (43.2 g, 0.2 mol), KCN (16.93 g, 0.26 mol), ammonium carbonate (40.59 g, 0.52 mol) and alcohol were reacted at 90°–110° C. for 71 hours. The workup on the hydantoin was in accordance with procedure L. Recrystallization of the acid insoluble product from methanol and acetone was followed by a base solubilization and acid precipitation yield of spiro-[2,7-difluorofluoren-9,4'-imidazolidine]-2',5'-dione (32.8 g, 0.115 mol), m/e+ 286 for $C_{15}H_8F_2N_2O_2$; m.p. 327°–329° dec.; and Calc. %C 62.94 %H 2.82 %F 13.28 %N 9.79, Obs. %C 62.78 %H 2.86 %F 13.05 %N 9.62.

PREPARATION N dl-Spiro-[2-carboxyfluoren-9,4'-imidazolidine]-2',5'-dione has the formula

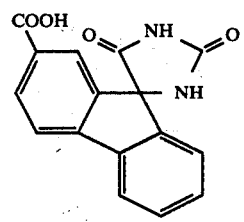

and may be prepared as follows.

2-Carboxyfluorenone (2.5 g, 11.2 mmol), KCN (1.5 g, 23 mmol), ammonium carbonate (4.4 g) and alcohol (50 mL) were heated at 105° C. in a glass pressure reactor overnight. The reaction mixture was poured into 5% HCl (100 mL) and the product filtered. The collected product was dissolved in 5% NaOH, refiltered and precipitated with acid. The filtered precipitate was washed with water and air dried having a m.p. 331°–332° C. dec $C_{16}H_{10}N_2O_4$ m/e+ 294.

PREPARATION O dl-Spiro-[3-chlorofluoren-9,4'-imidazolidine]-2',5'-dione has the formula

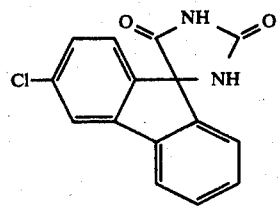

and may be prepared as follows.

N-2-(3-chloro-9-oxofluorenyl)trifluoroacetamide was prepared according to the procedure of H. Pan and T. L. Fletcher in *J. Med. Chem.* 7, (1964) 31–38. This ketone (3.25 g, 10 mmol) was refluxed in 20% hydrochloric acid (100 mL) for one hour and then cooled to 5° C. The amine was then diazotized with sodium nitrite (1.0 g, 1.5 equivalents). Cold 50% hypophosphorus acid (100 mL) then was slowly added. The mixture then was stored overnight at 5° C., then warmed to ambient temperature, diluted with water and extracted with benzene. Chromatography through alumina with benzene as an eluent yielded 3-chlorofluorenone (1.6 g). Yellow plates from ethanol had a m.p. 156°-158° C.; HRMS calc. 214.0185 for $C_{13}H_7ClO$, obs. 214.0188, error 0.3 mmu/1.4 ppm.

The ketone (1.5 g, 7 mmol), KCN (0.65 g, 10 mmol), ammonium carbonate (1.5 g) and 90% ethanol (60 ml) was placed in a stainless steel reaction vessel. The mixture was heated at 110°-115° C. for 12 hours. The reaction vessel was cooled and cold 10% hydrochloric acid was added. The triturated solid was collected by filtration. The resulting solid was dissolved in 5% sodium hydroxide, filtered and the filtrate was acidified with concentrated hydrochloric acid. The precipitated solid was collected by filtration and washed with cold water (1.1 g) yielding a product with a m.p. 330° C. dec.; HRMS calc. 284.0352 for $C_{15}H_9ClN_2O_2$, obs. 284.0364, 1.1 mmu/4.2 ppm.

PREPARATION P dl-Spiro-[2-methylthiofluoren-9,4'-imidazolidine]-2',5'-dione has the formula

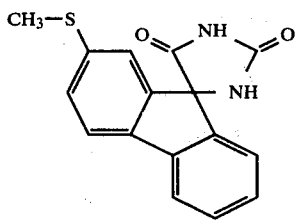

and may be prepared as follows.

The ketone, 2-methylthiofluorenone, was prepared by suspending sodium hydride (14.4 g of the 50% by weight mineral oil dispersion, 0.30 mol) in anhydrous dimethylformamide (400 mL). To this stirred suspension under an argon atmosphere was added methylmercaptan as a gas. After the solution was saturated with methylmercaptan and the sodium hydride reacted, the yellow 2-fluorofluorenone (30 g, 0.15 mol) was added in one portion. The resulting red solution was heated for four hours at 60°-80° C. Water (50 mL) was added and the solvent was removed with heat and reduced pressure. The red residue was dissolved in ethyl acetate (500 mL) and extracted with 0.1 N sodium hydroxide (3×200 mL). These extractions were followed by washes with 0.1 N hydrochloric acid (200 mL) and water (3×200 mL). The yellow-orange ethyl acetate solution then was treated with activated charcoal and anhydrous sodium sulfate. After filtration the ethyl acetate solution was evaporated with heat and reduced pressure to yield an orange solid which was triturated with hot hexanes (200 mL) and then allowed to cool. The ketone was collected by filtration (31.1 g, 91%), the product having a m.p. of 85° C. (reported 84°-85° C. by J. A. Parry and K. D. Warren, J. Chem. Soc. 1965, 4049-4054); PMR (CDCl$_3$, TMS): delta 2.4 (3H, methyl singlet); delta 6.95-7.7 (7H, aromatic multiplet); and m/e+ 226 for $C_{14}H_{10}OS$.

The ketone (22.6 g, 0.10 mol), KCN (13 g, 0.20 mol), ammonium carbonate (30 g) and absolute ethanol (approx. 120 mL) were heated in a 200 cc stainless steel pressure reactor for 15 hours at 105° C. After cooling the contents were poured with stirring onto ice (200 cc) and 5 N hydrochloric acid (100 mL). The resulting orange suspension then was collected by filtration onto sintered glass. The 1 N sodium hydroxide (250 mL) was filtered with stirring through the collected solid. The bright orange filtrate then was precipitated with concentrated hydrochloric acid and collected. The air dried precipitate then was dissolved in hot dimethylformamide (100 mL). The solution was treated with Darco G-60 (activated charcoal sold by Fischer Scientific Products for chromatography, 4 g) and filtered with the aid of Celite. Water (400 ml) and ice (100 cc) were added to the filtrate precipitating an off-white solid.

The collected precipitate was then redissolved in 1 N sodium hydroxide and treated as before with Darco G-60. After acidification the resulting white precipitate was collected and washed thoroughly with water and dried at 100° C. in a vacuum oven to yield dl-spiro-[2-methylthiofluoren-9,4'-imidazolidine]-2',5'-dione (18.6 g., 63%) with a m.p. 299°-300° C. dec.; HRMS for $C_{16}H_{12}N_2O_2S$ calc. 296.0619, obs. 296.0626, error 0.7 mmu/2.4 ppm; and PMR (DMSO-d6, TSP); delta 2.47 (3H, methyl); delta 7.0-8.8 (9H, aromatic and hydantoin multiplet); and elemental analysis: calc. %C 64.85 %H 4.08 %N 9.45 %S 10.82. obs. %C 64.89 %H 4.12 %N 9.44 %S 10.95.

PREPARATION Q

Spiro-[2-(R,S)-methylsulfinylfluoren-9,(R,S)4'-imidazolidine]-2',5'-dione has the formula

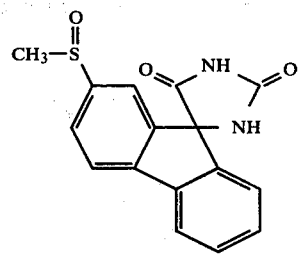

and the unresolved diastereomeric mixture of the four stereoisomers [(R,R),(R,S),(S,S),(S,R) isomers] may be prepared as follows.

The hydantoin product of procedure P(3.0 g, 10 mmol) was suspended in 50% acetone and water (100 mL) and sodium metaperiodate (2.25 g, 10.5 mmol) was added. This mixture was stirred at ambient temperature for 72 hours, whereupon 100 mL of 1 N hydrochloric acid were added and the suspension was filtered and washed thoroughly with water. The resulting solid was dissolved in 1 N NaOH (25 mL), filtered and the filtrate acidified with concentrated hydrochloric acid. Filtration and water washes yielded a white product (2.6 g, with drying at 100° C.) with a m.p. 284°-286° C. dec.; HRMS for $C_{16}H_{12}N_2O_3S$ calc. 312.0568 obs. 312.0565 error 0.3 mmu/1.0 ppm; and PMR (DMSO-d6, TSP): delta 2.84 (3H, methyl singlet), (9H, low field aromatic and hydantoin multiplet).

PREPARATION R dl-Spiro-(2-methylsulfonylfluoren-9,4'-imidazolidine)-2'5'-dione has the formula

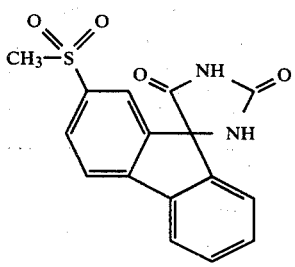

and may be prepared as follows.

The hydantoin product of procedure P (3.0 g, 10 mmol) was suspended in 50% acetone and water (100 mL), and sodium metaperiodate (6.42 g, 30 mmol) was added. This mixture was refluxed with stirring for 15 hours, whereupon 100 mL of 1 N hydrochloric acid and 100 cc of ice were added. The suspension was filtered and washed thoroughly with water and air dried. Further drying in a vacuum oven at 100° C. yielded a white fluffy product (3.1 g) with a m.p. 309°–311° C. dec.; HRMS for $C_{16}H_{12}N_2O_4S$ calc. 328.0518, obs. 328.0527 error 0.9 mmu/2.7 ppm; and PMR (DMSO-d6, TSP): delta 3.30 (3H, methyl singlet); (9H, low field aromatic and hydantoin multiplet).

PREPARATION S dl-Spiro-[1-fluorofluoren-9,4′-imidazolidine]-2′,5′-dione has the formula

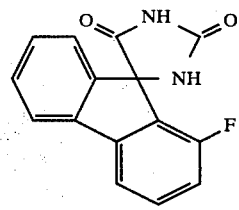

and may be prepared as follows.

1-Fluorofluorenone was prepared from 1-aminofluorenone (Pfaltz and Bauer, Inc.) by the procedure of T. L. Fletcher and M. J. Namkung, *Chemistry and Industry*, Feb. 11, 1961, pp. 179–180 which yielded a ketone product m.p. 109°–110° C., m/e+· 198 for $C_{13}H_7FO$.

1-Fluorofluorenone (3.96 g, 20 mmol), KCN (1.95 g, 30 mmol), ammonium carbonate (4.8 g) and 100% ethanol (100 ml) were reacted and a product (2.8 g) collected as in Preparation L, the product having a m.p. 338°–341° C. dec., HRMS for $C_{15}H_9FN_2O_2$ calc. 268.0648, obs. 268.0653 error 0.5 mmu/1.9 ppm.

PREPARATION T dl-Spiro-[3-flurofluoren-9,4′-imidazolidine]-2′,5′-dione has the formula

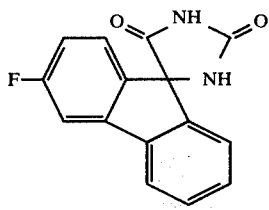

and may be prepared as follows.

3-Fluorofluorenone was prepared from 3-aminofluorenone by the procedure of T. L. Flectcher and M. J. Namkung, *Chemistry and Industry*, Feb. 11, 1961, pp. 179–180 and T. L. Fletcher et. al., *J. Org. Chem.*, 25, (1960) 1342 yielding the ketone product with a m.p. 129° C. and m/e+· 198 for $C_{13}H_7FO$. The preparation of the spiro hydantoin was otherwise as in Preparation L, (yield 3.1 g) the resulting product with a m.p. 328°–332° C. dec, and HRMS for $C_{15}H_9FN_2O_2$ calc. 268.0648, obs. 268.0653, error 0.5 mmu/1.9 ppm.

PREPARATION U dl-Spiro-[4-flurofluoren-9,4′-imidazolidine]-2′,5′-dione has the formula

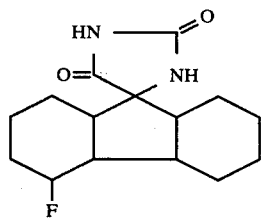

and may be prepared as follows.

4-Flourofluorenone was prepared from 4-aminofluorenone (Pfaltz and Bauer, Inc.) by the procedure of T. L. Flectcher and M. J. Namkung, *Chemistry and Industry*, Feb. 11, 1961, pp. 179–180 yielding the ketone product with a m.p. 160°–162° C. and m/e+· 198 for $C_{13}H_7FO$. The preparation of the spiro hydantoin was otherwise as in Preparation L (yield 3.0 g), the resulting product with a m.p. 330°–333° C. and HRMS for $C_{15}H_9FN_2O_2$ calc. 268.0648, obs. 268.0660, error 1.2 mmu/4.5 ppm.

PREPARATION V dl-Spiro-(4-aza-fluorene-9,4′-imidazolidine)-2′,5′ dione has the formula:

and may be prepared as follows.

4-Aza-9-fluorenone (Aldrich Chemical Co.), (2.4 g, 13.3 mmol), KCN (2.0 g, 30.7 mmol) and ammonium carbonate (5.0 g) in 80% ethanol (50 cc) were placed in a thick walled glass pressure reactor. The mixture was heated at 110°–115° C. for 12 hours. The reaction vessel was cooled and ice water (200 mL) was added to the reaction mixture. Dilute hydrochloric acid was added until pH was approximately 8 and the solid was collected by filtration. The collected solid was dissolved in 5% sodium hydroxide and treated with activated charcoal and filtered through a Celite (diatomaceous earth filter aid) pad. The solution was adjusted to pH 7–8 by the addition of 1 N hydrochloric acid. The resulting precipitate was collected on a filter, washed with cold water and dried to yield a sample of dl-Spiro-(4-aza-fluorene-9,4′-imidazolidine)-2′,5′-dione (1.4 g) having a melting point of 311°–312° C. with dec., m/e+ 251 for $C_{14}H_9N_3O_2$.

Preparations of dl-Spiro-(1,7-difluoro fluoren-9,4'-imidazolidine)-2',5'-dione; dl-spiro-(2,5-difluorofluoren-9,4'-imidazolidine)-2',5'-dione; dl-spiro-(2,6-difluorofluoren-9,4'-imidazolidine)-2',5'-dione, dlspiro-(2-fluoro-7-methylthiofluoren-9,4'-imidazolidine)-2',5'-dione; and spiro-(2-fluoro-7-methylsulfinylfluoren-9,4'-imidazolidine)-2',5'-dione.

dl-Spiro-(1,7-difluorofluoren-9,4'-imidazolidine)-2',5'-dione can be prepared from 1-fluorofluorene. dl-Spiro-(2,5-difluorofluoren-9,4'-imidazolidine)-2',5'-dione can be prepared from 4-fluorofluorene. dl-Spiro-(2,6-difluorofluoren-9,4'-imidazolidine)-2',5'-dione can be prepared from 3-fluorofluorene. These fluorene precursors, 1-fluorofluorene, 4-fluorofluorene and 3-fluorofluorene can be prepared via the Schiemann reaction from the corresponding amines, 1-aminofluorene, 4-aminofluorene and 3-aminofluorene, according to the procedure of T. L. Fletcher and M. L. Namkung, *Chemistry and Industry*, Feb. 11, 1961, pp. 179–180. The resulting 1-fluorofluorene, 4-fluorofluorene and 3-fluorofluorene derivatives can be nitrated in the 7 position using the general nitration method cited in *Org. Synthesis*, Coll. Vol 2, 447 (1943). The resulting nitro derivatives, 1-fluoro-7-nitrofluorene, 4-fluoro-7-nitrofluorene and 3-fluoro-7-nitrofluorene, can be reduced using the general reduction method cited in *Org. Synthesis*, Coll. Vol 5, 30 (1973) to yield 7-amino-1-fluorofluorene, 2-amino-5-fluorofluorene and 2-amino-6-fluorofluorene respectively. These amines employing the general procedure of T. L. Flectcher and M. L. Namkung, *Chemistry and Industry*, Feb. 11, 1961, pp. 179–180 can be transformed via the corresponding diazonium tetrafluoroborate salts into 1,7-difluorofluorene, 2,5-difluorofluorene and 2,6-difluorofluorene. These difluorofluorenes can be oxidized to the corresponding ketones using a general procedure of U. Sprinzak, *J. Amer. Chem. Soc.*, 80 (1958) or via procedures cited herein in Procedure L or M to yield: 1,7-difluorofluorenone; 2,5-difluorofluorenone; 2,6-difluorofluorenone. As in procedures L and M these ketones can be converted into the corresponding spiro-hydantoins: dl-spiro-(1,7-difluorofluoren-9,4'-imidazolidine)-2',5'-dione; dl-spiro-(2,5-difluorofluoren-9,4'-imidazolidine)-2',5'-dione; dl-spiro-(2,6-difluorofluoren-9,4'-imidazolidine)-2',5'-dione respectively.

dl-Spiro-(2-fluoro-7-methylthiofluoren-9,4'-imidazolidine)-2',5'-dione can be prepared from 2,7-difluorofluorenone. The 2,7-difluorofluorenone is reacted as in Procedure P except one equivalent of the sodium methylthiolate (prepared from sodium hydride and methylmercaptan) is employed. The resulting 2-fluoro-7-methylthiofluorenone is synthetically transformed as in procedure L or P to the desired racemic spiro-(2-fluoro-7-methylthiofluoren-9,4'-imidazolidine)-2',5'-dione.

The diastereomeric mixture of four stereoisomers of spiro-(2-fluoro-7-methylsulfinylfluoren-9,4'-imidazolidine)-2',5'-dione can be prepared according to the Procedure Q cited herein whereby racemic spiro-(2-fluoro-7-methylthiofluoren-9,4'-imidazolidine)-2',5'-dione is oxidized by sodium metaperiodate to yield the diastereomeric mixture of four stereoisomers of spiro-(2-fluoro-7-methylsulfinylfluoren-9,4'-imidazolidine)-2',5'-dione.

Compounds A to V were tested for their ability to inhibit aldose reductase enzyme activity via the procedure of P. F. Kador, L. O. Merola and J. H. Kinoshita as described in *Documenta Ophthamologica*, 18 (1979) 117. The results are shown in Table I, II and III.

TABLE I

| IC*$_{50}$-Human Aldose Reductase Inhibition Activity | |
|---|---|
| COMPOUND | IC$_{50}$ (Molar) |
| A (unsubstituted) | $1.2 \times 10^{-6}$ |
| L (dl-2-Fluoro) | $9.1 \times 10^{-8}$ |
| M (2,7-Difluoro) | $5.2 \times 10^{-8}$ |
| V (dl-Aza) | $6.5 \times 10^{-5}$ |
| Sarges Resolved** | $6.4 \times 10^{-7}$ |

*IC$_{50}$ = Concentration of drug that inhibits 50% of the enzyme activity
**Sarges Resolved Compound = d-Spiro-(6-fluorochroman-4,4'-imidazolidine)-2',5'-dione.

TABLE II

| IC*$_{50}$-Rat Aldose Reductase Inhibition Activity | |
|---|---|
| COMPOUND | IC$_{50}$ (Molar) |
| L (dl-2-Fluoro) | $1.5 \times 10^{-7}$ |
| M (2,7-Difluoro) | $4.4 \times 10^{-8}$ |
| P (dl-2-Methylthio) | $4.2 \times 10^{-7}$ |
| Q (dl-2-Methylsulfinyl) | $1.7 \times 10^{-6}$ |
| R (dl-2-Methylsulfonyl) | $5.0 \times 10^{-6}$ |
| S (dl-1-Fluoro) | $5.9 \times 10^{-7}$ |
| U (dl-4-Fluoro) | $4.6 \times 10^{-7}$ |
| Sarges Racemic** | $4.3 \times 10^{-7}$ |
| Sarges Resolved*** | $1.5 \times 10^{-7}$ |

*IC$_{50}$ = Concentration of drug that inhibits 50% of the enzyme activity.
**Sarges Racemic Compound = dl-Spiro-(6-fluorochroman-4,4'-imidazolidine)-2',5'-dione.
***Sarges Resolved Compound = d-Spiro-(6-fluorochroman-4,4'-imidazolindine)-2',5'-dione.

It is noteworthy that Compounds L and M are as active or more active against human aldose reductase than rat aldose reductase and hence more selective against human aldose reductase than rat aldose reductase when compared to the Sarges resolved compound. These agents will exhibit more activity in humans than the Sarges resolved compound. The Sarges resolved compound shows only one fourth as much activity against human aldose reductase as compared to its activity against rat aldose reductase. It is apparent on analysis of both in vitro and in vivo potency data described herein that compounds L and M will exhibit significantly greater relative potencies in humans against aldose reductase related diabetic complications. This is apparent from comparative studies cited herein on diabetic and glactosemic rats and in vitro human enzyme inhibition studies. Both the racemic 2-fluoro (L) and 2,7-difluoro (M) derivatives are 7X and 12X more active against human aldose reductase than the Sarges resolved compound. The Sarges resolved compound is found to be equiactive against rat aldose reductase to the racemic 2-fluoro and half as active as the 2,7-difluoro derivative in vitro, but both the 2-fluoro and 2,7-difluoro derivatives were found unexpectedly and significantly more active in vivo than the Sarges compound in rat studies.

TABLE III

| | In vitro Aldose Reductase Inhibition:* | | | | | |
|---|---|---|---|---|---|---|
| IC$_{50}$ | $10^{-4}$ | $10^{-5}$ | $10^{-6}$ | $10^{-7}$ | $10^{-8}$ | Species |
| A | 89 | 84 | 49 | 13 | — | Human |
| B | 65 | 30 | 12 | — | — | Human |
| C | 65 | 20 | 8 | — | — | Human |
| D | 100 | 76 | 20 | — | — | Human |
| E | 100 | 82 | 62 | 33 | 8 | Rat |
| F | — | 94 | 76 | 55 | 12 | Rat |
| G | 50 | 28 | 20 | — | — | Human |
| H | 3 | 31 | 0 | — | — | Human |
| I | 50 | 25 | 10 | — | — | Human |

TABLE III-continued

| | In vitro Aldose Reductase Inhibition:* | | | | | |
|---|---|---|---|---|---|---|
| $IC_{50}$ | $10^{-4}$ | $10^{-5}$ | $10^{-6}$ | $10^{-7}$ | $10^{-8}$ | Species |
| J | 94 | 88 | 77 | 39 | 0 | Human |
| K | 96 | 85 | 47 | 6 | — | Rat |
| L | 100 | 88 | 81 | 53 | 18 | Human |
| M | — | 81 | 71 | 64 | 35 | Human |
| N | 89 | 54 | 0 | — | — | Rat |

*According to the procedures of P. F. Kador and N. E. Sharpless, Biophysical Chemistry, 8 (1978) 81-85; P. F. Kador, L. O. Merola and J. H. Kinoshita Documenta Ophthamologica, 18 (1979) 117.

In Vivo Evaluations

A. The effect of dl-spiro-(2-fluorofluorene-9,4'-imidazolidine)-2',5'-dione and spiro(2,7-difluoro-fluoren-9,4'-imidazolidine)-2',5'-dione on the prevention on retardation of cataracts in rats was studied using the unresolved dl-spiro-(6-fluorochroman-4,4'-imidazolidine)-2',5'-dione based upon Sarges U.S. Pat. No. 4,117,230. The compounds were formulated in ground Purina Rodent Laboratory Chow, Number 5001, containing 30% galactose.

Eighty-four rats were divided into the following seven groups (six treated groups having different compound intake levels and an untreated galactose control) having different compound intake levels as shown in Table IV.

TABLE IV

| Test Compound Dosages | |
|---|---|
| COMPOUND | Mg INTAKE/Kg BODYWEIGHT/DAY |
| L (2-fluoro) Racemic | 4 Mg/Kg/day |
| L (2-fluoro) Racemic | 8 Mg/Kg/day |
| M (2,7-difluoro) | 4 Mg/Kg/day |
| M (2,7-difluoro) | 8 Mg/Kg/day |
| Sarges Racemic | 4 Mg/Kg/day |
| Sarges Racemic | 8 Mg/Kg/day |
| Galactose CONTROL | — |

The galactose control group (twelve rats, twenty-four eyes) were fed ground Purina Rodent Laboratory Chow, No. 5001 containing 30% by weight galactose. The six test compound groups (twelve rats, twenty-four eyes per group) were fed the same 30% galactose chow except that the chow was formulated to deliver mg/kg/day of the indicated test compound (see Table IV.).

It is known that young male rats fed a 30% galactose diet (As previously described) will develop lenticular changes within several days which predicatively progress in time irreversibly to cataracts. Aldose reductase inhibitor compounds which are in vivo active will delay or prevent galactose induced cataractogenesis. In this in vivo experiment, the test aldose reductase inhibitor compounds were formulated in the 30% galactose feed to evaluate their in vivo anticataract activity. The 168 rat eyes of the eighty-four rats were observed for the following conditions over a 32 day period.

| | DESCRIPTION |
|---|---|
| Normal | Normal lens, no vacuoles |
| Time to begin cataract formation | Vacuoles just beginning to appear around lens perimeter |
| Time to vacoule | Vacuolization clearly visible on anterior lens surface |
| Time to snowflake | Small opaque "flecks" grossly visible in addition to vacuoles |
| Time to nuclear | Nuclear cataract; interior |
| cataract | lens completely opaque |

Observations were made at days 2, 3, 4, 5, 6, 8, 10, 12, 14, 16, 18, 20, 22, 24, 26, 28, 30 and 32.

All rat eyes in treatment L (2-fluoro) groups and M (2,7-diluoro) groups were asymptomatic at the end of 32 days. All rat eyes in the Sarges groups developed snowflake-like opacities without any indication of earlier vacuole formation. The average time to snowflake-like opacities was 15.7 days for the Sarges Racemic 4 Mg/Kg group and 19.7 days for the Sarges Racemic 8 Mg/Kg group. This difference is statistically ($p<0.05$) significant. Rat eyes in the galatose control group followed the usual pattern of cataract formations. The average time to snowflake was 11.5 days. This was statistically ($p<0.05$) significantly lower than the average for either Sarges group.

The "time to cataract" is summarized in Table V.

TABLE V

| | Times to Cataract | | |
|---|---|---|---|
| Treatment | Range (days) | Mean (day) | Standard Deviation |
| Sarges Racemate 4 Mg/Kg/day | 12 to 22 | 15.68 | 2.68 |
| Sarges Racemate 8 Mg/Kg/day | 14 to 30 | 19.68 | 4.68 |

The "time to cataract" is on the average 4 days less for Sarges Racemic 4 Mg/Kg/day compound than for the Sarges Racemic 8 Mg/Kg/day compound. This difference is statistically significant at the 95% probability level.

Rat eyes in the galactose control group followed the usual pattern of cataract formation. The times to each type of cataract activity are summarized in Table VI.

TABLE VI

| | Times to Cataract for Galactose Control | | |
|---|---|---|---|
| Stage | Range (days) | Mean (day) | Standard Deviation |
| Time to early vacoules | 3 to 4 | 3.58 | 0.50 |
| Time to vacoules | 4 to 10 | 6.00 | 2.00 |
| Time to snowflake | 8 to 18 | 11.50 | 2.30 |
| Time to nuclear cataract | 16 to 32 | 24.04 | 6.52 |

All but 3 rat eyes (12.5%) developed nuclear cataracts by Day 32. The time to nuclear is estimated as 35 days for these three rats in the computation of the mean and standard deviation.

At Day 32, three rats were selected and sacrificed at random from the groups treated with the racemic 2-fluoro derivative at 4 Mg/Kg/day, the racemic 2-fluoro derivative 8 Mg/Kg/day, 2,7-difluoro derivative 4 Mg/Kg/day, 2,7-difluoro derivative at 8 Mg/Kg/day and the Sarges Racemic compound at 4 and 8 Mg/Kg/day, and the dulcitol levels in the lenses were measured.

The average galactitol levels for Sarges Racemic at 4 Mg/Kg/day and Sarges Racemic derivative at 8 Mg/Kg/day were 9.238 and 9.107 respectively, and are statistically ($p<0.05$) significantly greater than the averages for the racemic 2-fluoro derivative at 4

Mg/Kg/day and the racemic 2-fluoro derivative at 8 Mg/Kg/day, 6.274 and 5.074 respectively, and the averages for 2,7-difluoro derivative at 4 and 8 Mg/Kg/day 2.560 and 1.399 respectively. The average galactitol levels for both doses of the 2,7-difluoro derivative are statistically ($p<0.05$) less than the average for either dose of the racemic 2-fluoro compound. Both the racemic 2-fluoro and the 2,7-difluoro derivatives inhibit cataract development. The 2,7-difluoro derivative is more potent than the 2-fluoro compound. A dose response relationship is observed between the 4 and the 8 mg racemic 2-fluoro compound.

B. In vivo dose response studies were conducted to test the in vivo dose activity of the following compounds by intubation (per oral) in galactocemic rats on a 30% galactose diet previously described:

L*  dl-Spiro-[2-fluorofluoren-9,4'-imidazolidine]-2',5'-dione

M  Spiro-[2,7-difluorofluoren-9,4'-imidazolidine]-2',5'-dione; and

Sarges  dl-Spiro-[6-fluorochroman-4,4'-imidazolidine]-2,5'-dione.

* Compound L and Sarges Racemic are racemic.

Stock suspensions of the test compounds and all dilutions of the compound were formulated with 0.03% by weight Tween 80.

Experimental Design

Healthy, Charles River CD (outbred albino, Sprague-Dawley derived) male rats, aged 20-30 days, without observable ocular defects and ranging in weight from 35-45 grams, were acclimated to experimental conditions (in quarantine) for two days prior to beginning the study.

Rats were individually assigned to one of twenty-three groups according to a random number schedule. Two rats, belonging to the same drug-diet treatment group, were housed per cage. Treatment and control groups consisted of six (6) rats each with no replacement in the event of death, and were designated as follows:

| Group | No. Rats | Drug Dose (mg/kg) | Doses/ Day | No. Days |
|---|---|---|---|---|
| Sarges Racemic$_A$ | 6 | 40.000 | 1 | 14 |
| Sarges Racemic$_B$ | 6 | 12.600 | 1 | 14 |
| Sarges Racemic$_C$ | 6 | 4.000 | 1 | 14 |
| Sarges Racemic$_D$ | 6 | 1.260 | 1 | 14 |
| Sarges Racemic$_E$ | 6 | 0.400 | 1 | 14 |
| Sarges Racemic$_F$ | 6 | 0.126 | 1 | 14 |
| Sarges Racemic$_G$ | 6 | 0.040 | 1 | 14 |
| 2-fluoro (L)$_A$* | 6 | 40.000 | 1 | 14 |
| 2-fluoro (L)$_B$* | 6 | 12.600 | 1 | 14 |
| 2-fluoro (L)$_C$* | 6 | 4.000 | 1 | 14 |
| 2-fluoro (L)$_D$* | 6 | 1.260 | 1 | 14 |
| 2-fluoro (L)$_E$* | 6 | 0.400 | 1 | 14 |
| 2-fluoro (L)$_F$* | 6 | 0.126 | 1 | 14 |
| 2-fluoro (L)$_G$* | 6 | 0.040 | 1 | 14 |
| Difluoro (M)$_A$ | 6 | 40.000 | 1 | 14 |
| Difluoro (M)$_B$ | 6 | 12.600 | 1 | 14 |
| Difluoro (M)$_C$ | 6 | 4.000 | 1 | 14 |
| Difluoro (M)$_D$ | 6 | 1.260 | 1 | 14 |
| Difluoro (M)$_E$ | 6 | 0.400 | 1 | 14 |
| Difluoro (M)$_F$ | 6 | 0.126 | 1 | 14 |
| Difluoro (M)$_G$ | 6 | 0.040 | 1 | 14 |
| Positive Galuctosemic Vehicle Control** | 6 | 0.000 | 1 | 14 |
| Positive Galactosemic Control | 6 | 0.000 | 0 | 14 |

*Racemic
**This group was given an average dose of vehicle based on body weight.

Lenses of all eyes were examined with a hand-held ophthalmoscope in the early stages of cataract development and a penlight for the stages, snowflake-like, snowflake, and nuclear cataract. Lens grading occurred every day for the first ten study days, and then every other day until study Day 14.

The test was to determine the relative efficacy and potency of the dl-2-fluoro and 2,7-difluoro compounds in terms of equal amounts of test drug per kg of body weight relative to Sarge's dl-spiro-[6-fluorochroman-4,4'-imidazolidine]-2',5'-dione, the positive anticataract control.

The relative potency determination was made at 7 drug levels over half log dose intervals. The response (percent cataracts formed and/or the time to cataract formation) was plotted against mg/kg and/or moles/kg.

Assumptions on Experimental Design

The study was directed to the suppression and/or elimination of the initial stages of cataract development characterized by vacuoles or snowflake-like opacities only. It was assumed therefore that suppression and/or elimination of vacuoles or lens opacification by the test drugs affects the transport, absorption and/or metabolism of galactose in such a manner as to prevent subsequent osmotic disturbances normally leading to tissue degeneration and advanced cataract. Advanced cataract defined as stages 2-4 of the Sipple classification was assumed to be of secondary importance to the etiology of cataract inhibition.

In the event where cataract stage other than vacuole formed, such as snowflake-like opacities, this cataract was counted similarly as vacuole in percent cataract formation.

Studies demonstrate that 90% of young rats (50 gram) fed to a 30% galactose diet will develop vacuole cataracts within 5-7 days. This study yielded this expected effect in the control groups.

Experimental Procedures

All animals were fed Purina Laboratory Chow and water, ad libitum, for the two day acclimation period. All drugs were dosed orally by intubation using an animal feeding needle (Popper and Sons), 18 or 20 gauge, attached to a 1 or 3 ml syringe. Once the dosing time schedule was established, the schedule was followed throughout the study to compensate for any diurnal variation.

The animals were kept on a twelve hour day/night cycle. The temperature and humidity were determined each day at the scheduled dosing time of 1:00 p.m.

The animals were weighed every other day and adjustments to dosage amounts to compensate for weight gain were made each day prior to the dose time. All food was routinely withheld from all animal groups for four hours (9:00 a.m.) prior to the drug dose and restored two hours (3:00 p.m.) post-dose. Otherwise sufficient amounts of chow or diet mixture were maintained in the food hopper to allow the animals to eat ad libitum. There were two days of drug dosage with the animals remaining on Purina Laboratory Chow (Days 1 and 2). The 30% galactose diet mixture was introduced to the animals two hours post-dose on Day 3 which constituted Day 1 of the study.

Ocular Examination and Grading

All eyes were examined with a hand-held ophthalmoscope and/or penlight at the times designated in the Experimental Design section.

It has been found in previous studies that dilation of the eye with a mydriactic (i.e. Mydriacyl) is not necessary for accurate grading, due to the semi-transparent nature of the rat iris. In the early stages (i.e., grades —, ±, and +) the lens was observed by reflecting the ophthalmoscope beam off the retina back through the lens and iris. Using this technique, vacuoles appear as dark, almost opaque patches. In the latter opacity stages (grades SL, S and N) the lens were observed grossly with a penlight. Eacy eye was given one of the following grades:

| Grade | Description |
|---|---|
| — | Normal lens, no vacuoles |
| ± | Vacuoles just beginning around lens perimeter |
| + | Vacuoles cover greater than ½ of lens surface |
| S | Lens completely opaque; small opaque "flecks" visible in lens |
| N | Nuclear cataract; white crystalline material present in lens center |
| SL | Small opaque "flecks" visible with no vacuoles present (snowflake-like) |

Statistical Analysis

The percent of eyes with vacuoles (cataracts) and/or the time to vacuole formation were analyzed for each treatment/concentration group. Since the data were sufficient, the potency of the 2,7-difluoro and racemic 2-fluoro compounds relative to the control were estimated by a probit analysis or other appropriate methodology.

TABLE VII

Sarges Racemic* Versus Examples L (Racemic 2-fluoro) and M (2,7-difluoro)

| Drug | Dose (mg/kg) | Day 0 | 1 | 2 | 3 | 4 | 5 | 6 | 7 | 8 | 9 | 10 | 12 | 14 |
|---|---|---|---|---|---|---|---|---|---|---|---|---|---|---|
| Sarges Racemic | 40 | 0 | 0 | 0 | 0 | 0 | 0 | 0 | 0 | 0 | 0 | 0 | 0 | 0% |
| 2-fluoro** | 40 | 0 | 0 | 0 | 0 | 0 | 0 | 0 | 0 | 0 | 0 | 0 | 0 | 0 |
| 2,7-difluoro | 40 | 0 | 0 | 0 | 0 | 0 | 0 | 0 | 0 | 0 | 0 | 0 | 0 | 0 |
| Sarges Racemic | 12.6 | 0 | 0 | 0 | 0 | 0 | 0 | 0 | 0 | 0 | 0 | 0 | 0 | 8 |
| 2-fluoro** | 12.6 | 0 | 0 | 0 | 0 | 0 | 0 | 0 | 0 | 0 | 0 | 0 | 0 | 0 |
| 2,7-difluoro | 12.6 | 0 | 0 | 0 | 0 | 0 | 0 | 0 | 0 | 0 | 0 | 0 | 0 | 0 |
| Sarges Racemic | 4.0 | 0 | 0 | 0 | 0 | 0 | 0 | 0 | 0 | 0 | 0 | 0 | 17 | 50 |
| 2-fluoro** | 4.0 | 0 | 0 | 0 | 0 | 0 | 0 | 0 | 0 | 0 | 0 | 0 | 0 | 0 |
| 2,7-difluoro | 4.0 | 0 | 0 | 0 | 0 | 0 | 0 | 0 | 0 | 0 | 0 | 0 | 0 | 0 |
| Sarges Racemic | 1.26 | 0 | 0 | 0 | 0 | 0 | 0 | 0 | 0 | 8 | 17 | 83 | 100 | 100 |
| 2-fluoro** | 1.26 | 0 | 0 | 0 | 0 | 0 | 0 | 0 | 0 | 0 | 0 | 0 | 0 | 0 |
| 2,7-difluoro | 1.26 | 0 | 0 | 0 | 0 | 0 | 0 | 0 | 0 | 0 | 0 | 0 | 0 | 0 |
| Sarges Racemic | 0.4 | 0 | 0 | 0 | 0 | 0 | 0 | 33 | 33 | 50 | 58 | 83 | 83 | 100 |
| 2-fluoro** | 0.4 | 0 | 0 | 0 | 0 | 0 | 0 | 0 | 8 | 42 | 42 | 67 | 83 | 100 |
| 2,7-difluoro | 0.4 | 0 | 0 | 0 | 0 | 0 | 0 | 0 | 0 | 0 | 0 | 0 | 0 | 0 |
| Sarges Racemic | 0.126 | 0 | 0 | 0 | 0 | 0 | 0 | 33 | 33 | 50 | 58 | 83 | 83 | 100 |
| 2-fluoro** | 0.126 | 0 | 0 | 0 | 0 | 0 | 0 | 33 | 33 | 50 | 50 | 50 | 83 | 83 |
| 2,7-difluoro | 0.126 | 0 | 0 | 0 | 0 | 0 | 0 | 8 | 25 | 67 | 67 | 67 | 67 | 75 |
| Galactose Control | | 0 | 0 | 0 | 0 | 0 | 0 | 33 | 50 | 100 | 100 | 100 | 100 | 100 |
| Vehicle/Galactose | | 0 | 0 | 0 | 0 | 0 | 0 | 17 | 58 | 83 | 83 | 83 | 100 | 100 |

% = Percent eyes with cataracts formed.
Cataract is defined as distinct vacuoles or opacities which affect the transparency of the lens or the lens ability to transmit light without significant light scatter.
*dl-Spiro-[6-fluorochroman-4,4'-imidazolidine]-2',5'-dione which is a Pfizer aldose reductase inhibitor.
**Racemic The same data as in Table VII may be illustrated in a different format.

TABLE VIII

Percent of Rat Eyes (n = 12) With at Least Vacuoles Formed

| | Day 6 | Day 7 | Day 8 | Day 9 | Day 10 | Day 12 | Day 14 |
|---|---|---|---|---|---|---|---|
| Sarges Racemic | | | | | | | |
| 40.000 | 0.0% | 0.0% | 0.0% | 0.0% | 0.0% | 0.0% | 0.0% |
| 12.600 | 0.0% | 0.0% | 0.0% | 0.0% | 0.0% | 0.0% | 0.3% |
| 4.000 | 0.0% | 0.0% | 0.0% | 0.0% | 0.0% | 16.7% | 50.0% |
| 1.260 | 0.0% | 0.0% | 8.3% | 16.7% | 83.3% | 100.0% | 100.0% |
| 0.400 | 33.3% | 33.3% | 50.0% | 58.3% | 83.3% | 83.3% | 100.0% |
| 0.126 | 33.3% | 33.3% | 41.7% | 75.0% | 100.0% | 100.0% | 100.0% |
| 0.040 | 0.0% | 8.3% | 50.0% | 66.7% | 100.0% | 100.0% | 100.0% |
| Racemic 2-fluoro (L) | | | | | | | |
| 40.000 | 0.0% | 0.0% | 0.0% | 0.0% | 0.0% | 0.0% | 0.0% |
| 12.600 | 0.0% | 0.0% | 0.0% | 0.0% | 0.0% | 0.0% | 0.0% |
| 4.000 | 0.0% | 0.0% | 0.0% | 0.0% | 0.0% | 0.0% | 0.0% |
| 1.260 | 0.0% | 0.0% | 0.0% | 0.0% | 0.0% | 0.0% | 0.0% |
| 0.400 | 0.0% | 8.3% | 41.7% | 41.7% | 66.7% | 83.3% | 100.0% |
| 0.126 | 33.3% | 33.3% | 50.0% | 50.0% | 50.0% | 83.3% | 83.3% |
| 0.040 | 33.3% | 50.0% | 83.3% | 83.3% | 100.0% | 100.0% | 100.0% |

TABLE VIII-continued 2,7-difluoro (M)

| | | | | | | | |
|---|---|---|---|---|---|---|---|
| 40.000 | 0.0% | 0.0% | 0.0% | 0.0% | 0.0% | 0.0% | 0.0% |
| 12.600 | 0.0% | 0.0% | 0.0% | 0.0% | 0.0% | 0.0% | 0.0% |
| 4.000 | 0.0% | 0.0% | 0.0% | 0.0% | 0.0% | 0.0% | 0.0% |
| 1.260 | 0.0% | 0.0% | 0.0% | 0.0% | 0.0% | 0.0% | 0.0% |
| 0.400 | 0.0% | 0.0% | 0.0% | 0.0% | 0.0% | 0.0% | 0.0% |
| 0.126 | 8.3% | 25.0% | 66.7% | 66.7% | 66.7% | 66.7% | 75.0% |
| 0.040 | 50.0% | 66.7% | 83.3% | 83.3% | 91.7% | 100.0% | 100.0% |
| Vehicle Control | 33.3% | 50.0% | 100.0% | 100.0% | 100.0% | 100.0% | 100.0% |
| Untreated Control | 16.7% | 58.3% | 83.3% | 83.3% | 83.3% | 100.0% | 100.0% |

At observation day 12, the log relative potencies for eyes with vacuoles or more advanced cataracts with their 95% confidence limits are:

| | Log Potency | (95% Confidence Limits) |
|---|---|---|
| 2-fluoro* (L) relative to Sarges Racemic | 0.6605 | (0.3889 to 0.9346) |
| 2,7-difluoro (M) relative to Sarges Racemic | 1.1114 | (0.8501 to 1.3852) |
| 2,7-difluoro (M) relative to 2-fluoro* (L) | 0.4473 | (0.1898 to 0.7144). |

The antilogs of the relative potencies with their 95% confidence limits are:

| | Relative Potency | (95% Confidence Limits |
|---|---|---|
| 2-fluoro* (L) relative to Sarges Racemic | 4.58 | (2.45 to 8.60) |
| 2,7-difluoro (M) relative to Sarges Racemic | 12.92 | (7.08 to 24.28) |
| 2,7-difluoro (M) relative to 2-fluoro* (L) | 2.80 | (1.55 to 5.18) |

*Racemic

C. Polyol Accumulation in Diabetic Rat Lens and Sciatic Nerves

As a further test of the efficacy of the racemic 2-fluoro and the 2,7-difluoro compound versus the Sarges Resolved compound, observation was made of the in vivo inhibition of polyol accumulation in the sciatic nerve and lens of rats with streptozotocin induced diabetic rats. The basis and techniques of the experiment are described in "Polyol Accumulation In Nervous Tissue Of Rats With Experimental Diabetes And Galactosaemia", M. A. Steward, W. R. Sherman, Mary M. Kurien, G. I. Moonsammy and M. Wisgerhof, *Journal of Neuorchemistry*, 14 (1967) 1057–1066.

In the test, eight male Sprague-Dawley rats weighing about 150 g were fasted overnight and given an injection of streptozotocin the next day. The dose was 9–10 mg/100 g of animal weight in an acid citrate buffer diluted in normal saline. The injection was given in or near the tail vein.

The respective aldose reductase inhibitors (the Sarges Revolved, racemic 2-fluoro, and 2,7-difluoro compounds) were given to 4 of the rats at 4, 8 and 24 hours. The dose of 0.15 mg/100 g animal weight was given orally in about 5 μl of water. Each inhibitor was mixed in an erude suspension of water with a mortar and pestle. An aliquot of this mixture was then taken, using an automatic pipet and fed to each animal.

On the day following the streptozotocin injection, the blood glucose of the animals was determined using the glucose oxidase-peroxidase method. At 27 hours all the animals were sacrificed and the lenses and sciatic nerves were removed, weighed and homogenized. These homogenates were then analyzed for sorbitol content using the GLC method. The experimental group (which was fed the inhibitor) was compared with the controls (not fed inhibitor) and the percentage of inhibition was determined. Each value represents comparison of 4 values for control and 4 for experimental. The results of the test are shown in Table IX.

TABLE IX

In vivo Inhibition of Polyol Accumulation in the Sciatic Nerve and Lens of Streptozotocin Induced Diabetic Rats

| Compound | mg/deciliter Average Blood Glucose* | Percent Inhibition Nerve | Percent Inhibition Lens |
|---|---|---|---|
| Sarges Resolved** | 298 ± 17 | 77% | 83% |
| Racemic 2-fluoro (L) | 425 ± 39 | 96% | 92% |
| 2,7-difluoro (M) | 349 ± 32 | 90–95% | 95% |

*Eight animals were used for each study, 4 control, 4 experimental.
**d-Spiro-[6-fluorochroman-4,4'-imidazolidine]-2',5'-dione

D. Nerve Conduction Study In Diabetic Rats

The purpose is to evaluate the efficacy of the racemic 2-fluoro compound (L), an aldose reductase inhibitor, for inhibiting cataractogenesis and nerve conduction deficit in diabetic rats.

Methods and Materials

Diabetes was induced in male albino rats by the intravenous injection of 50 mg/kg streptozotocin. The diabetic state was verified by measuring the blood glucose level in each animal before and after injection. Diabetic animals were assigned randomly to three groups as follows: (1) vehicle treated control; (2) 8 mg/kg the racemic 2-fluoro compound (L); and (3) 16 mg/kg Sarges Racemic. A fourth group consisted of non-diabetic and otherwise normal rats which remained untreated. Treatments were given once daily by oral lavage, and continued through the day prior to sacrifice of the animal.

Each animal was weighed on a weekly basis. Both lenses of each animal were examined by ophthalmoscope periodically and any cataractous changes were graded and noted. At the end of 15 weeks, each animal was anesthetized using pentobarbital and the nerve conduction velocities of the sciatic nerve were measured. After an animal was sacrificed, the sciatic nerve and other tissues and organs were taken, weighed, and frozen for future biochemical analyses.

Results

Cataractous changes were graded on a scale of 0 to 4; 0 denoting a normal looking lens with no changes and 4 denoting opacification involving the whole lens. The lenses of those rats in the untreated, normal control group exhibited no apparent changes and remained optically clear. Of the 32 lenses (16 rats) present at the end of 15 weeks in the vehicle-treated diabetic rats, 27 had a score of 4, 3 scored 3, and 2 scored 2 on cataractous changes. Thus, every lens exhibited maximal or near maximal opacity. Racemic 2-fluoro compound (L) was effective in preventing opacification of the lens in diabetic rats. Of 30 lenses (15 rats) in the Sarges Racemic-treated group, all appeared normal. Thus, both compounds were effected for preventing cataracts in diabetic rats at 8 mg/kg of the racemic 2-fluoro compound and 16 mg/kg of the Sarges Racemic compound.

The record of electrical activity from the sciatic nerve in response to electrical stimulation of the nerve exhibited two inflections and two peaks, probably representing different nerve fiber groups. The effect of treatment on each of the four events was determined, and all are considered, although treatment effects appear to be greatest on the first inflection. By comparison to the normal, untreated controls, the conduction velocities determined for the vehicle-treated, diabetic rats were as follows: first inflection, 83% of normal; first peak, 82% of normal; second inflection, 80.6% of normal; and, second peak, 76.4% of normal. Thus, the impairment of nerve conduction, as manifest by a reduction in velocity of conduction, ranged from 17% to 23.6% and is attributable to the diabetic state of these animals. In those rats (diabetic) treated with the racemic 2-fluoro compound (L), the nerve conduction velocities as a percent of normal were as follows: first inflection, 93.3%; first peak, 88.2%; second inflection, 87.4%; and second peak, 85.0%. In these animals, then, the impairment ranged from 6.7% to 15%, representing an improvement by treatment of 34% to 61%. In those diabetic rats treated with Sarges Racemic, the nerve conduction velocities as a percent of normal were as follows: first inflection, 88.6%; first peak, 83.9%; second inflection, 82.4%; second peak, 79.1%. This represents an impairment ranging from 11.4% to 20.9%, indicating an improvement over controls of 9% to 33%. Therefore, both the racemic 2-fluoro compound (L) and Sarges Racemic produce some beneficial effect to improve nerve conduction velocity and return it towards normal. However, the racemic 2-fluoro compound (L), at one-half the dose of Sarges Racemic, allows a greater improvement. Statistical analysis indicates that only the improvement by the racemic 2-fluoro compound (L) is significant, by comparison to the untreated diabetic rats.

It should be understood that while certain preferred embodiments of the present invention have been illustrated and described, various modifications thereof will become apparent to those skilled in the art. Accordingly, the scope of the present invention should be defined by the appended claims and equivalents thereof.

Various features are set forth in the following claims.
What is claimed is:

1. A method for treating diabetic complications in mammals comprising administering an effective amount of spiro-(fluoren-9,4'-imidazolidine)-2',5'-dione or pharmaceutically acceptable salt thereof having the formula

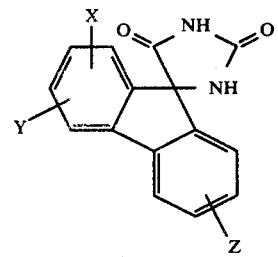

where
x = H, F, Cl, Br, I, $SCH_3$, $S(O)CH_3$, $S(O_2)CH_3$, $OCH_3$ and $CH_3$,
y = H, F, Cl, Br, I, $SCH_3$, $S(O)CH_3$, $S(O_2)CH_3$, $OCH_3$ and $CH_3$, and
z = H, F, Cl, Br, I, $OCH_3$ and $CH_3$.

2. A method as recited in claim 1 wherein said complication is diabetic cataract.

3. A method as recited in claim 1 wherein said complication is neuropathy.

4. A method as recited in claim 1 wherein said complication is retinopathy.

5. A method as recited in claim 1 wherein said complication is nephropathy.

6. A method in accordance with claims 1, 2, 3, 4 or 5 wherein said spiro-(fluoren-9,4'-imidazolidine)-2',5'-dione has the formula

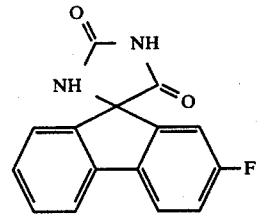

7. A method in accordance with claims 1, 2, 3, 4 or 5 wherein said spiro-(fluoren-9,4'-imidazolidine)-2',5'-dione has the formula.

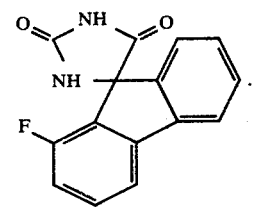

8. A method in accordance with claims 2, 3, 4 or 5 wherein said spiro-(fluoren-9,4'-imidazolidine)-2',5'-dione has the formula

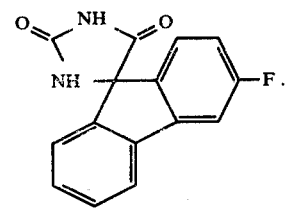

9. A method in accordance with claims 1, 2, 3, 4 or 5 wherein said spiro-(fluoren-9,4'-imidazolidine)-2',5'-dione has the formula

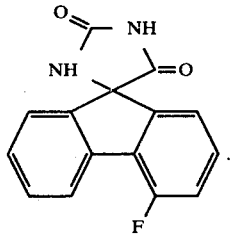

10. A method in accordance with claims 1, 2, 3, 4 or 5 wherein said spiro-(fluoren-9,4'-imidazolidine)-2',5'-dione has the formula

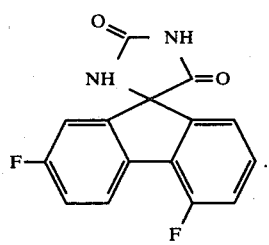

11. A method in accordance with claims 1, 2, 3, 4 or 5 wherein said spiro-(fluoren-9,4'-imidazolidine)-2',5'-dione has the formula

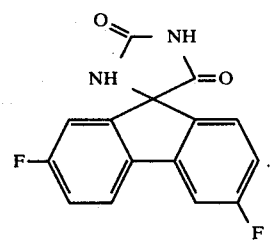

12. A method in accordance with claims 1, 2, 3, 4 or 5 wherein said spiro-(fluoren-9,4'-imidazolidine)-2',5'-dione has the formula

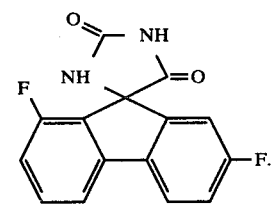

13. A method in accordance with claims 1, 2, 3, 4 or 5 wherein said spiro-(fluoren-9,4'-imidazolidine)-2',5'-dione has the formula

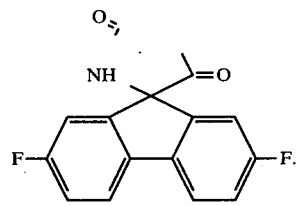

14. A method in accordance with claims 1, 2, 3, 4 or 5 wherein said spiro-(fluoren-9,4'-imidazolidine)-2',5'-dione has the formula

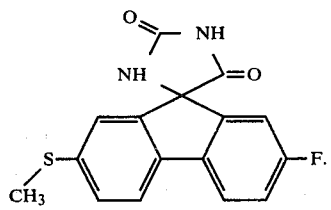

15. A method in accordance with claims 1, 2, 3, 4 or 5 wherein said spiro-(fluoren-9,4'-imidazolidine)-2',5'-dione has the formula

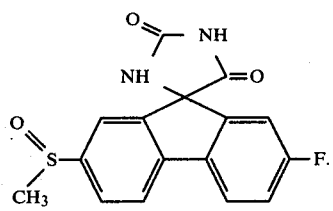

16. A method in accordance with claims 1, 2, 3, 4 or 5 wherein said spiro-(fluoren-9,4'-imidazolidine)-2',5'-dione has the formula

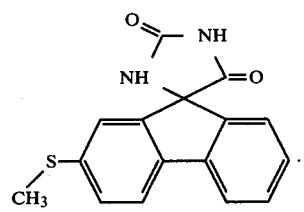

17. A method in accordance with claims 1, 2, 3, 4 or 5 wherein said spiro-(fluoren-9,4'-imidazolidine)-2',5'-dione has the formula

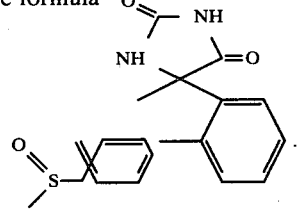

18. A method in accordance with claims 1, 2, 3, 4 or 5 wherein said spiro-(fluoren-9,4'-imidazolidine)-2',5'-dione has the formula

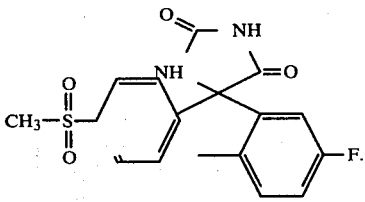

* * * * *

UNITED STATES PATENT AND TRADEMARK OFFICE
CERTIFICATE OF CORRECTION

PATENT NO. : 4,436,745

DATED : March 13, 1984

INVENTOR(S) : Billie M. York, Jr.

It is certified that error appears in the above-identified patent and that said Letters Patent is hereby corrected as shown below:

Column 1, line 61, "methythio" should read --methylthio--.

Column 3, lines 6-7, "spiro-(2,7-difluroxanthen-9,4'-imidazolidine)" should read --spiro-(2,7-difluoroxanthen-9,4'-imidazolidine)--.

Column 4, lines 25-34 (Preparation D), the Formula should appear as follows:

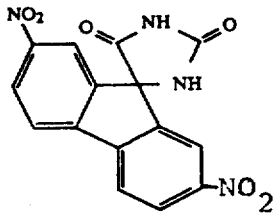

Column 5, line 36, "Pocedure" should read --Procedure--.

UNITED STATES PATENT AND TRADEMARK OFFICE
CERTIFICATE OF CORRECTION

PATENT NO. : 4,436,745

DATED : March 13, 1984

INVENTOR(S) : Billie M. York, Jr.

It is certified that error appears in the above-identified patent and that said Letters Patent is hereby corrected as shown below:

Column 6, lines 28-37, the Formula should appear as follows:

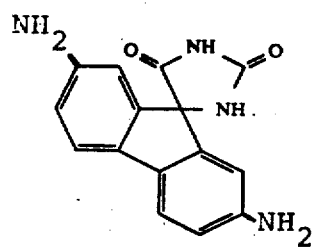

Column 7, line 51, "fluorboric" should read --fluoroboric--.

Column 14, line 10, "dec" should read --dec.--.

Column 14, lines 16-26, the Formula should appear as follows:

UNITED STATES PATENT AND TRADEMARK OFFICE
CERTIFICATE OF CORRECTION

PATENT NO. : 4,436,745

DATED : March 13, 1984

INVENTOR(S) : Billie M. York, Jr.

It is certified that error appears in the above-identified patent and that said Letters Patent is hereby corrected as shown below:

Column 14, line 28, "4-Flourofluorenone" should read --4-Fluorofluorenone--.

Column 14, line 30, "Flectcher" should read --Fletcher--.

Column 15, line 6, after "dione" insert a semi-colon (;); change "dlspiro" to --dl-spiro--.

Column 15, line 32, "Flectcher" should read --Fletcher--.

Column 16, line 29, "imidazolindine" should read --imidazolidine--.

Column 16, line 47, "glactosemic" should read --galactosemic--.

Column 16, line 68, Table III, "3" should read --43--. ($10^{-4}$ Column).

Column 18, line 9, "(2,7-diluro)" should read --(2,7-difluoro)--.

Column 18, line 16, "galatose" should read --galactose--.

Column 20, line 44, after "fed" delete "to".

Column 21, line 19, "Eacy" should read --Each--.

UNITED STATES PATENT AND TRADEMARK OFFICE
CERTIFICATE OF CORRECTION

PATENT NO. : 4,436,745

DATED : March 13, 1984

INVENTOR(S) : Billie M. York, Jr.

It is certified that error appears in the above-identified patent and that said Letters Patent is hereby corrected as shown below:

Column 23, line 40, "Steward" should read --Stewart--.

Column 23, line 42, "Neuorchemistry" should read --Neurochemistry--.

Column 23, line 50, "Revolved" should read --Resolved--.

Column 26, line 55, "Claims 2, 3, 4, or 5" should read --Claims 1, 2, 3, 4, or 5--.

Column 28, lines 1-9, the Formula should read as follows:

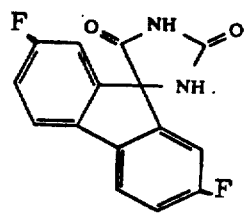

UNITED STATES PATENT AND TRADEMARK OFFICE
CERTIFICATE OF CORRECTION

PATENT NO. : 4,436,745

DATED : March 13, 1984

INVENTOR(S) : Billie M. York, Jr.

It is certified that error appears in the above-identified patent and that said Letters Patent is hereby corrected as shown below:

Column 28, lines 47-54, the Formula should read as follows:

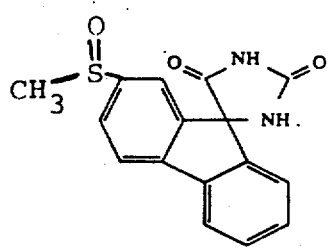

UNITED STATES PATENT AND TRADEMARK OFFICE
CERTIFICATE OF CORRECTION

PATENT NO. : 4,436,745

DATED : March 13, 1984

INVENTOR(S) : Billie M. York, Jr.

It is certified that error appears in the above-identified patent and that said Letters Patent is hereby corrected as shown below:

Column 28, lines 58-67, the Formula should read as follows:

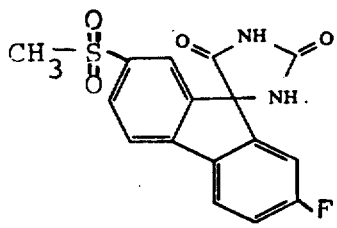

Signed and Sealed this

Fifth Day of November 1985

[SEAL]

Attest:

Attesting Officer

DONALD J. QUIGG

Commissioner of Patents and Trademarks